United States Patent [19]

Hata et al.

[11] Patent Number: 4,780,556
[45] Date of Patent: Oct. 25, 1988

[54] METHOD FOR PRODUCING CHLOROSILANES

[75] Inventors: Kazuhiko Hata; Yoshinori Kobayashi; Toshiro Ohishi; Katsuhisa Masumoto; Masaru Kamoda; Tetsuo Murata, all of Niihama, Japan

[73] Assignee: Sumitomo Chemical Company, Limited, Osaka, Japan

[21] Appl. No.: 150,902

[22] Filed: Feb. 1, 1988

[30] Foreign Application Priority Data

Feb. 6, 1987 [JP] Japan .................. 62-26760
Feb. 6, 1987 [JP] Japan .................. 62-26761
Mar. 24, 1987 [JP] Japan .................. 62-70939

[51] Int. Cl.$^4$ .............................. C07F 7/08
[52] U.S. Cl. ................... 556/467; 556/477
[58] Field of Search ................ 556/467, 477

[56] References Cited

U.S. PATENT DOCUMENTS

| | | | |
|---|---|---|---|
| 2,500,761 | 3/1950 | Lewis | 556/467 |
| 2,615,034 | 10/1952 | Hyde | 556/467 |
| 3,689,519 | 9/1972 | LeFort | 556/467 X |
| 3,718,682 | 2/1973 | Bakassian et al. | 556/467 |
| 4,310,680 | 1/1982 | Kötzsch et al. | 556/467 |
| 4,417,067 | 11/1983 | Kötzsch et al. | 556/467 |

FOREIGN PATENT DOCUMENTS

| | | | |
|---|---|---|---|
| 0163435 | 12/1985 | European Pat. Off. | 556/467 |
| 3013920 | 10/1981 | Fed. Rep. of Germany | 556/467 |
| 3133885 | 3/1983 | Fed. Rep. of Germany | 556/467 |
| 47-005020 | 2/1972 | Japan | 556/477 X |
| 52-144628 | 11/1977 | Japan | 556/477 X |
| 53-147030 | 8/1978 | Japan | 556/477 X |
| 55-092392 | 4/1980 | Japan | 556/477 X |
| 62-010095 | 3/1987 | Japan | 556/477 X |
| 62-145092 | 8/1987 | Japan | . |

OTHER PUBLICATIONS

J. Amer. Chem. Soc., 70, 433, 434, (1948).
Chemical Abstract, 74, 58908w, 1971.
J. Organometallic Chem., 275, pp. C1–C4, (1984).

Primary Examiner—Paul F. Shaver
Attorney, Agent, or Firm—Stevens, Davis, Miller & Mosher

[57] ABSTRACT

A method for producing chlorosilanes, which are useful in a wide range of industrial field as an intermediate for organosilicon products such as silicone rubbers, silicone oils, silicone resins, etc. as well as a raw material for the production of organic chemicals such as medicines, agricultural chemicals, dyestuffs, etc., represented by the general formula,

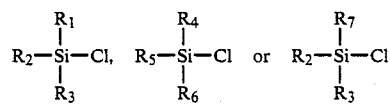

wherein $R_1$ and $R_4$, which may be the same or different, represent an alkyl group having from 1 to 5 carbon atoms, a chloromethyl group, an ethynyl group or a halogen atom; $R_2$ and $R_3$, which may be the same or different, represent an alkyl group having from 1 to 3 carbon atoms; $R_5$ and $R_6$, which may be the same or different, represent an alkyl group having from 1 to 2 carbon atoms; and $R_7$ represents an alkyl group having from 1 to 18 carbon atoms, which comprises reacting a disiloxane represented by the general formula,

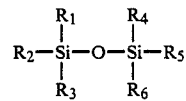

wherein $R_1$, $R_2$, $R_3$, $R_4$, $R_5$ and $R_6$ are as defined above, or a silanol represented by the general formula,

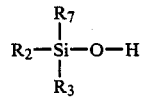

wherein $R_2$, $R_3$ and $R_7$ are as defined above, with phosgene in the presence or absence of a tertiary amide.

6 Claims, No Drawings

METHOD FOR PRODUCING CHLOROSILANES

The present invention relates to a method for producing chlorosilanes from disiloxanes or silanols.

Chlorosilanes are important compounds used in a wide range of industrial field as an intermediate for organosilicon products such as silicone rubbers, silicone oils, silicone resins, etc. as well as a raw material for the production of organic chemicals such as medicines, agricultural chemicals, dyestuffs, etc.

The following methods are known as a method for producing chlorosilanes from disiloxanes or silanols.

(1) A method of reacting disiloxanes with sulfuric acid and ammonium chloride [J. Am. Chem. Soc., 70, 433, 445 (1948)].

(2) A method of reacting disiloxanes with hydrogen chloride (JP-A-No. 52-144628 and JP-A-No. 55-92392).

(3) A method of reacting disiloxanes with thionyl chloride in the presence of a strong inorganic acid (JP-B-No. 56,-19355).

(4) A method of reacting disiloxanes or silanols with dimethylhalogenosilane in the presence of an inorganic iron compound (JP-B-No. 57-7639).

(5) A method of reacting silanols with hydrogen chloride (Chemical Abstract, Vol. 74, 58908w).

(6) A method of reacting silanols with phosphorus pentachloride [Journal of Organometallic Chemistry, Vol. 275, pp. C1–C4 (1984)].

In the foregoing well-known methods, however, the reaction temperature is high or low so that the reaction is carried out under industrially disadvantageous conditions, and besides it produces unnecessary by-products and in some cases, causes a problem of environmental preservation, for example treatment of waste liquors produced by treatment after reaction. These methods are not therefore satisfactory.

In view of the situation like this, the present inventors have extensively studied a method for producing chlorosilanes from disiloxanes or silanols in an industrially advantageous manner, and as a result, have found that by reacting disiloxanes or silanols with phosgene in the presence or absence of a tertiary amide, chlorosilanes can be produced selectively and in a high yield under mild conditions. The present inventors thus completed the present invention.

The present invention provides a method for producing chlorosilanes represented by the general formula,

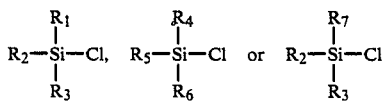

wherein $R_1$ and $R_4$, which may be the same or different, represent an alkyl group having from 1 to 5 carbon atoms, a chloromethyl group, an ethynyl group or a halogen atom; $R_2$ and $R_3$, which may be the same or different, represent an alkyl group having from 1 to 3 carbon atoms; $R_5$ and $R_6$, which may be the same or different, represent an alkyl group having from 1 to 2 carbon atoms; and $R_7$ represents an alkyl group having from 1 to 18 carbon atoms, which comprises reacting a disiloxane represented by the general formula,

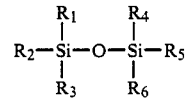

wherein $R_1$, $R_2$, $R_3$, $R_4$, $R_5$ and $R_6$ are as defined above, or a silanol represented by the general formula,

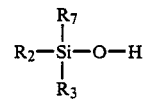

wherein $R_2$, $R_3$ and $R_7$ are as defined above, with phosgene in the presence or absence of a tertiary amide.

Disiloxanes used in the present invention include hexamethyldisiloxane, hexaethyldisiloxane, bis-chlorotetramethyldisiloxane, triethyltripropyldisiloxane, bischloromethyltetramethyldisiloxane, bisethynyltetramethyldisiloxane, dibutyltetramethyldisiloxane, etc. Silanols include triethylsilanol, trimethylsilanol, tributylsilanol, tripropylsilanol, ethyldimethylsilanol, diethylmethylsilanol, tert-butyldimethylsilanol, diethylpropylsilanol, hexyldimethylsilanol, decyldimethylsilanol, tetradecyldimethylsilanol, octadecyldimethylsilanol, etc. The disiloxanes and silanols, however, are not limited to these examples.

These disiloxanes and silanols are available, but disiloxanes or silanols obtained as by-product from chlorosilanes which are used to protect or activate a functional group in the production of organic chemicals, can also be used.

For the tertiary amide used in the present invention, N,N-dialkylcarboxylic acid amides are generally used, and they include N,N-dimethylformamide, N,N-diethylformamide, N-methyl-N-phenylformamide, N,N-diphenylformamide, N,N-dimethylacetamide, high molecular compounds having these acid amides in the side chain, etc. The rate of reaction is so large that, among these acid amides, N,N-dimethylformamide and N-methyl-N-phenylformamide are preferably used, and N,N-dimethylformamide is particularly preferably used.

Generally, the amount of the tertiary amide used is about 0.001 mole or more, preferably 0.01 mole or more, particularly preferably 0.02 mole or more per 1 equivalent of the silicon-oxygen bond in the disiloxanes or silanols. Since the tertiary amide has also the function of solvent, the upper limit of its amount is not particularly limited. When the amount is less than about 0.001 mole, a long period of time is necessary to complete the reaction so that such amount is not preferred. When promotion only of the reaction is desired, amounts of from about 0.01 to about 0.2 mole are usually used.

In the reaction of phosgene with disiloxanes or silanols, in order to convert all the silicon-oxygen bonds in the disiloxanes or silanols to a silicon-chlorine bond, 1 equivalent or more of phosgene is necessary per 1 equivalent of the silicon-oxygen bond.

Excess phosgene remains unreacted after reaction, so that to use more phosgene than required is not preferred because a great deal of labor is necessary to recover the phosgene.

When the presence of phosgene left unreacted is not desired, the amount of phosgene may be decreased to 1 equivalent or less.

In this case, all phosgene supplied to reaction is consumed to produce the desired product.

Usually, from about 0.8 to about 1.2 equivalent of phosgene is used per 1 equivalent of the silicon-oxygen bond in the disiloxanes or silanols.

The reaction of the present invention is generally carried out in the presence of a solvent, but it may be carried out without a solvent.

The solvent used in this reaction includes aromatic hydrocarbons (e.g. benzene, toluene, xylene, monochlorobenzene, dichlorobenzene), aliphatic hydrocarbons (e.g. cyclohexane, hexane, n-heptane, n-octane, methylcyclohexane, isooctane), ethers (e.g. diethyl ether, dibutyl ether), esters (e.g. ethyl acetate, butyl acetate), acid amides (e.g. N,N-dimethylformamide, N-methyl-N-phenylformamide), halogenated lower hydrocarbons (e.g. chloroform, 1,2-dichloroethane, 1,1,1-trichloroethane, 1,1,2-trichloroethane, tetrachloroethylene), etc.

The reaction is carried out at a temperature of generally from about 0° to about 100° C., preferably from 20° to 70° C.

When the reaction temperature exceeds about 100° C., the yield lowers because of the decomposition of the tertiary amide, and when it is lower than 0° C., the rate of reaction slows down to take a long time for completion of the reaction. Such temperatures are not therefore preferred.

The reaction pressure may be any of increased pressure and reduced pressure, but usually, the reaction is carried out in the vicinity of normal pressure.

The reaction may be carried out in any of a continuous form, semi-continuous form and batch form.

Generally, the reaction is carried out by introducing phosgene into a mixture prepared by previously mixing a disiloxane or silanol, a tertiary amide and if necessary, a solvent.

By subjecting the reaction solution obtained by the foregoing reaction to the well-known operations such as distillation, etc., the desired chlorosilane can easily be separated from others, i.e. the starting materials such as a disiloxane or silanol, phosgene, a tertiary amide and a solvent and by-products.

The separated tertiary amide and solvent can repeatedly be used in the reaction.

According to the method of the present invention wherein phosgene is reacted with disiloxanes or silanols in the presence or absence of a tertiary amide, the reaction can be carried out under a mild condition and chlorosilanes can be produced in high yields as compared with the conventionally employed methods. Further, because by-products can easily be separated by operations such as distillation, etc., chlorosilanes of high purity can easily be produced. Also, in the production of organic chemicals, the present invention is useful to recover chlorosilanes from disiloxanes or silanols which are produced as by-products from the chlorosilanes used for the purpose of protection, etc. of a functional group.

The present invention will be illustrated more specifically with reference to the following examples, but it is not limited to these examples.

EXAMPLE 1

To a glass reactor equipped with a gas supply pipe, reflux condenser, thermometer and stirrer were added 81.1 g (0.5 mole) of hexamethyldisiloxane and 306 g of 1,2-dichloroethane, and 98.9 g (1 mole) of phosgene was introduced into the resulting mixture at a temperature of from 50° to 55° C. over 9 hours with stirring.

After completion of the introduction, stirring was continued at the same temperature for further 3 hours, after which the reaction mixture was distilled to obtain 56.0 g of trimethylchlorosilane.

Boiling point: 56°–57° C.
Yield: 51.5%.

EXAMPLE 2

To the same reactor as used in Example 1 were added 81.1 g (0.5 mole) of hexamethyldisiloxane, 306 g of 1,2-dichloroethane and 18.3 g (0.25 mole) of N,N-dimethylformamide, and 74.0 g (0.748 mole) of phosgene was introduced into the resulting mixture at a temperature of from 40° to 45° C. over 2 hours with stirring. After completion of the introduction, the reaction mixture was separated from the catalyst layer and distilled to obtain 105.2 g of trimethylchlorosilane.

Boiling point: 56°–57° C.
Yield: 96.8%.

EXAMPLE 3

To the same reactor as used in Example 1 were added 1,2-dichloroethane and the catalyst layer separated in Example 2, and 81.1 g (0.5 mole) of hexamethyldisiloxane was added dropwise at a temperature of from 40° to 45° C. with stirring. Thereafter, 49.0 g (0.495 mole) of phosgene was introduced into the resulting mixture at the same temperature over 2 hours with stirring. After completion of the introduction, the same procedure as in Example 2 was carried out to obtain 105.6 g of trimethylchlorosilane.

Boiling point: 56°–57° C.
Yield: 97.1%.

EXAMPLE 4

To the same reactor as used in Example 1 were added 81.1 g (0.5 mole) of hexamethyldisiloxane, 1160 g of 1,2-dichloroethane and 6.76 g (0.05 mole) of N-methyl-N-phenylformamide, and 54.4 g (0.55 mole) of phosgene was introduced into the resulting mixture at a temperature of from 40° to 45° C. over 2 hours with stirring. After completion of the introduction, stirring was continued at the same temperature for 3 hours, and the same procedure as in Example 2 was carried out to obtain 102.1 g of trimethylchlorosilane.

Boiling point: 56°–57° C.
Yield: 94.0%.

EXAMPLE 5

To the same reactor as used in Example 1 were added 61.6 g (0.25 mole) of hexaethyldisiloxane, 250 g of 1,2-dichloroethane and 0.73 g (0.01 mole) of N,N-dimethylformamide, and 26.7 g (0.26 mole) of phosgene was introduced into the resulting mixture at a temperature of from 60° to 65° C. over 4 hours with stirring. After completion of the introduction, stirring was continued at the same temperature for 2 hours. Thereafter, the reaction mixture was distilled to obtain 71.3 g of triethylchlorosilane.

Boiling point: 144°–145° C.
Yield: 94.6%.

EXAMPLE 6

To the same reactor as used in Example 1 were added 24.7 g (0.1 mole) of 1,3-di-tert-butyl-1,1,3,3-tetramethyldisiloxane, 150 g of chloroform and 0.73 g (0.01 mole) of N,N-dimethylformamide, and 11.9 g (0.12 mole) of phosgene was introduced into the resulting mixture at a temperature of from 45° to 50° C. over 3 hours with stirring. After completion of the introduction, stirring was continued at the same temperature for 2 hours. Thereafter, the reaction mixture was distilled to obtain 26.7 g of tert-butyldimethylchlorosilane.

Boiling point: 124°–126° C.
Yield: 88.6%.

EXAMPLE 7

To the same reactor as used in Example 1 were added 66.1 g (0.5 mole) of tert-butyldimethylsilanol, 265 g of 1,2-dichloroethane and 18.3 g (0.25 mole) of N,N-dimethylformamide, and 74.0 g (0.748 mole) of phosgene was introduced into the resulting mixture at a temperature of from 40° to 45° C. over 2 hours with stirring. After completion of the introduction, the reaction mixture was distilled to obtain 72.4 g of tert-butyldimethylchlorosilane.

Boiling point: 124°–126° C.
Yield: 96.0%.

EXAMPLE 8

To the same reactor as used in Example 1 were added 66.2 g (0.5 mole) of triethylsilanol, 250 g of 1,2-dichloroethane and 3.65 g (0.05 mole) of N,N-dimethylformamide, and 54.4 g (0.55 mole) of phosgene was introduced into the resulting mixture at a temperature of from 40° to 45° C. over 2 hours with stirring. After completion of the introduction, the same procedure as in Example 7 was carried out to obtain 71.6 g of triethylchlorosilane.

Boiling point: 144°–145° C.
Yield: 95%.

EXAMPLE 9

To the same reactor as used in Example 1 were added 66.1 g (0.5 mole) of tert-butyldimethylsilanol, 950 g of 1,2-dichloroethane and 6.76 g (0.05 mole) of N-methyl-N-phenylformamide, and 54.4 g (0.55 mole) of phosgene was introduced into the resulting mixture at a temperature of from 40° to 45° C. over 2 hours with stirring. After completion of the introduction, stirring was continued at the same temperature for 3 hours, and the same procedure as in Example 7 was carried out to obtain 69.3 g of tert-butyldimethylchlorosilane.

Boiling point: 124°–125° C.
Yield: 92%.

EXAMPLE 10

To the same reactor as used in Example 1 were added 40.1 g (0.25 mole) of hexyldimethylsilanol, 160 g of 1,2-dichloroethane and 1.83 g (0.025 mole) of N,N-dimethylformamide, and 27.2 g (0.275 mole) of phosgene was introduced into the resulting mixture at a temperature of from 40° to 45° C. over 2 hours with stirring. After completion of the introduction, the same procedure as in Example 7 was carried out to obtain 40.7 g of hexyldimethylchlorosilane.

Boiling point: 77°–80° C./16 Torr.
Yield: 91%.

EXAMPLE 11

To the same reactor as used in Example 1 were added 54.1 g (0.25 mole) of decyldimethylsilanol, 215 g of 1,2-dichloroethane and 1.83 g (0.025 mole) of N,N-dimethylformamide, and 27.2 g (0.275 mole) of phosgene was introduced into the resulting mixture at a temperature of from 40° to 45° C. over 2 hours with stirring. After completion of the introduction, the same procedure as in Example 7 was carried out to obtain 51.7 g of decyldimethylchlorosilane.

Boiling point: 103°–106° C./1 Torr.
Yield: 88%.

EXAMPLE 12

To the same reactor as used in Example 1 were added 82.2 g (0.25 mole) of octadecyldimethylsilanol, 330 g of 1,2-dichloroethane and 1.83 g (0.025 mole) of N,N-dimethylformamide, and 27.2 g (0.275 mole) of phosgene was introduced into the resulting mixture at a temperature of from 40° to 45° C. over 2 hours with stirring. After completion of the introduction, the same procedure as in Example 7 was carried out to obtain 75.5 g of octadecyldimethylchlorosilane.

Boiling point: 184°–186° C./0.2 Torr.
Yield: 87%.

What is claimed is:

1. A method for producing chlorosilanes represented by the general formula,

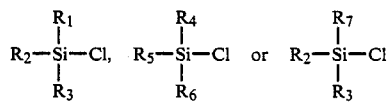

wherein $R_1$ and $R_4$, which may be the same or different, represent an alkyl group having from 1 to 5 carbon atoms, a chloromethyl group, an ethynyl group or a halogen atom; $R_2$ and $R_3$, which may be the same or different, represent an alkyl group having from 1 to 3 carbon atoms; $R_5$ and $R_6$, which may be the same or different, represent an alkyl group having from 1 to 2 carbon atoms; and $R_7$ represents an alkyl group having from 1 to 18 carbon atoms, which comprises reacting a disiloxane represented by the general formula,

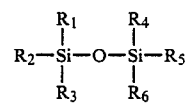

wherein $R_1$, $R_2$, $R_3$, $R_4$, $R_5$ and $R_6$ are as defined above, or a silanol represented by the general formula,

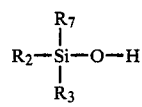

wherein $R_2$, $R_3$ and $R_7$ are as defined above, with phosgene in the presence or absence of a tertiary amide.

2. A method for producing chlorosilanes according to claim 1, wherein the disiloxane is hexamethyldisiloxane, hexaethyldisiloxane and 1,3-di-tert-butyl-1,1,3,3-tetramethyldisiloxane.

3. A method for producing chlorosilanes according to claim 1, wherein the silanol is tert-butyldimethylsilanol.

4. A method for producing chlorosilanes according to claim 1, wherein the tertiary amide is N,N-dimethylformamide or N-methyl-N-phenylformamide.

5. A method for producing chlorosilanes according to claim 1, wherein the amount of the tertiary amide added is 0.001 mole or more per 1 equivalent of the silicon-oxygen bond in the disiloxane or silanol.

6. A method for producing chlorosilanes according to claim 1, wherein the reaction temperature is from 0° to 100° C.

* * * * *